(12) United States Patent
Trogolo et al.

(10) Patent No.: US 8,063,116 B2
(45) Date of Patent: *Nov. 22, 2011

(54) ANTIMICROBIAL POWDER COATINGS AND METHOD

(75) Inventors: Jeffrey A. Trogolo, Boston, MA (US); Edward K. Welch, II, Naples, FL (US)

(73) Assignee: Sciessent LLC, Wakefield, MA (US)

( * ) Notice: Subject to any disclaimer, the term of this patent is extended or adjusted under 35 U.S.C. 154(b) by 318 days.

This patent is subject to a terminal disclaimer.

(21) Appl. No.: 11/895,330

(22) Filed: Aug. 24, 2007

(65) Prior Publication Data

US 2008/0051493 A1  Feb. 28, 2008

Related U.S. Application Data (60) Provisional application No. 60/840,286, filed on Aug. 25, 2006.

(51) Int. Cl.
| | |
|---|---|
| C09D 5/16 | (2006.01) |
| C08K 9/00 | (2006.01) |
| C08K 3/10 | (2006.01) |
| C08K 3/22 | (2006.01) |
| C08K 3/18 | (2006.01) |
| B32B 5/16 | (2006.01) |

(52) U.S. Cl. ........ 523/122; 523/204; 523/205; 524/403; 524/431; 524/432; 428/407; 428/457

(58) Field of Classification Search ................... 523/122, 523/204, 205; 524/403, 431, 432; 428/407, 428/457

See application file for complete search history.

(56) References Cited

U.S. PATENT DOCUMENTS

| | | | |
|---|---|---|---|
| 4,629,645 | A | 12/1986 | Inoue |
| 4,663,359 | A | 5/1987 | Rei |
| 5,180,585 | A | 1/1993 | Jacobson et al. |
| 5,187,220 | A | 2/1993 | Richart et al. |
| 5,238,749 | A | 8/1993 | Cueman et al. |
| 5,603,987 | A | 2/1997 | Lisenko |
| 5,639,550 | A | 6/1997 | Lisenko |
| 5,980,620 | A | 11/1999 | Brodie et al. |
| 6,093,407 | A | 7/2000 | Cummings et al. |
| 6,113,979 | A | 9/2000 | Sagawa et al. |
| 6,129,782 | A | 10/2000 | Brodie et al. |
| 6,432,416 | B1 | 8/2002 | Cummings et al. |
| 2003/0096017 | A1 | 5/2003 | Decker et al. |
| 2003/0141620 | A1 | 7/2003 | Stevenson et al. |
| 2004/0180098 | A1 | 9/2004 | Decker et al. |

FOREIGN PATENT DOCUMENTS

| | | |
|---|---|---|
| EP | 1034224 | 1/2005 |
| GB | 2297552 | 8/1996 |
| JP | 63239205 | 10/1988 |
| JP | 8060036 | 3/1996 |
| JP | 08199089 A2 | 8/1996 |
| JP | 08217998 A2 | 8/1996 |
| JP | 8239598 | 9/1996 |
| JP | 9263715 | 10/1997 |
| JP | 10168346 | 6/1998 |
| JP | 10316899 A2 | 12/1998 |
| WO | WO94/11446 | 5/1994 |
| WO | WO97/46626 | 12/1997 |
| WO | WO98/13429 | 4/1998 |
| WO | WO99/18162 | 4/1999 |

*Primary Examiner* — Kriellion Sanders (74) *Attorney, Agent, or Firm* — Edward K. Welch, II; IP & L Solutions (57) ABSTRACT

An improved method for fixedly coating powder coating pre-polymer and/or polymer particles with microparticles of solid, heat absorbing polymer additive materials, especially antimicrobial additive materials.

20 Claims, 1 Drawing Sheet

ANTIMICROBIAL POWDER COATINGS AND METHOD

1. RELATED APPLICATION

This patent application claims the benefit of previously filed U.S. Provisional Patent Application No. 60/840,286 entitled "Antimicrobial Powder Coatings and Method" filed on Aug. 25, 2006, which is hereby incorporated herein in its entirety by reference.

2. TECHNICAL FIELD

The present invention is directed to an improved method of preparing powder coatings having, as a component thereof, microparticles of a solid, heat absorbing material. In particular, the present invention is directed to an improved method of preparing antimicrobial prepolymer and/or polymer powder coatings. The improved method involves heating, preferably individually heating, the prepolymer and/or polymer powder particles and the microparticles of the solid material to temperatures whereby when the two are in intimate contact with one another, they will fuse to each other, but not to themselves.

3. DESCRIPTION OF THE PRIOR ART

The use of antimicrobial agents as additives for polymer compositions and coatings is well known. While molding compositions and liquid coatings have received the greatest attention, more recent attention has been focused on antimicrobial powder coatings and to articles treated therewith. For example, Cueman et. al. (U.S. Pat. No. 5,238,749) prepared amorphous thermoplastic and dual thermoplastic/thermoset powder coating compositions having incorporated therein a heavy metal-free antimicrobial agent and applied the same to a substrate by electrostatic, fluidized bed or flame spraying techniques. The antimicrobial agent was either incorporated into the thermoplastic or thermoset material, dry blended with the same or, in the case of flame-spraying, two streams, one of the polymer powder and one of the particulate antimicrobial agent were concurrently directed through the flame and to the surface so that they mix as they were deposited. Here, antimicrobial activity was reliant upon the migration of these organic antimicrobial agents from and through the amorphous zones of the polymer until equilibrium of the antimicrobial agent's internal vapor pressure was reached. Cueman et. al., however, required the use of organic antimicrobial agents which are heat sensitive and present great concern for human and environmental health and safety as well as resistance build up in the microbes to be attacked.

Clover et. al. (WO97/46626 and UK 2,297,552) teach powder coating compositions, especially polyester or epoxy-polyester based powder coating compositions, which inhibit the growth of bacteria as a result of the inclusion of a biocide into the powder coating composition. The biocide may be compounded into the powder coating materials or particles of the biocide of similar size to those of the powder coating material itself are intimately mixed (dry blended) before application.

Similarly, Cummings et. al. (U.S. Pat. No. 6,093,407 and EP 1034224) teach biocidal powder coating compositions wherein liquid and select solid biocidal agents, which do not react with other components of the powder coating compositions, are incorporated into the powder coating composition at the premix stage by extrusion blending, solution blending, or impact fusion. A subsequent Continuation-in-Part application of Decker et. al. (US 2003/1096017) characterized impact fusion was a fusion bonding process resulting from the prolonged, high speed dry mixing of the antimicrobial agent and the powder coating polymer particles. Specifically, the prolonged high speed mixing is said to induce an elevation in the temperature of the mixture to approximately the glass transition temperature of the polymer powder whereby the force of the mixing and the softening of the polymer powder particles causes the solid antimicrobial agent to fuse to the polymer particle surface. Unfortunately, particle fusion is indiscriminate and many of the polymer particles fuse to one another as well, thereby necessitating screening and further milling of the fused particles to return them to their free state.

While antimicrobial powder coatings have found commercial use and success, they have many shortcomings, especially insofar as inorganic antimicrobial agents, particularly those based Ion antimicrobial metal I and metal ions, are concerned. Unlike typical organic antimicrobial agents, which have comparatively high vapor pressures and/or migrate or bloom when employed in polymer materials, inorganic antimicrobial agents, especially those based-on antimicrobial metal and metal ions, rely upon surface exposure and/or a transport mechanism, typically an aqueous based transport mechanism, to deliver the antimicrobial active. Such transport mechanism is especially critical for the antimicrobial metal ion ion-exchange type antimicrobial agents. This is fine and good in hydrophilic, especially highly hydrophilic, materials where water absorbed by the hydrophilic polymer provides a transport mechanism for the antimicrobial agent through and within the bulk of the hydrophilic polymer. However, in the case of hydrophobic and poorly hydrophilic polymers, antimicrobial activity is limited to that-amount of antimicrobial agent at the surface of the finished polymer material due to the inaccessibility or, relative to the poorly hydrophilic polymers, the slow or poor accessibility of the antimicrobial agent within the bulk of the polymer. Consequently, that quantity of antimicrobial agent which is in the bulk of the polymer and not present at an exposed surface of the so formed or treated article or substrate is generally unavailable to contribute to the overall antimicrobial activity of the treated article or substrate.

Ideally, particularly with hydrophobic and poorly hydrophilic coatings, the thickness of the coating would be the same as the diameter of the antimicrobial additive in order to attain the greatest or optimal antimicrobial performance. However, given the small particle size of most antimicrobial additives, such powder coating thicknesses are neither typical nor feasible in most applications. Consequently, as the coating becomes thicker, relative to the particle size of the antimicrobial agent, more and more of the antimicrobial agent is incorporated into or entombed within the bulk of the polymer matrix. That portion of the antimicrobial agent within the bulk of the polymer only becomes available as the surface of the polymer coating wears away or is eroded, thereby exposing the previously entombed antimicrobial agent particles. If the erosion is too slow, the rate at which the antimicrobial agent becomes exposed may be too slow to provide any sufficient bioefficacy. If no such wear or erosion exists, then the entombed antimicrobial agent is truly wasted.

The foregoing issues are especially problematic in view of the fact that the vast majority of end use applications for powder coating compositions do not allow for the use of hydrophilic, especially highly hydrophilic, polymers. Rather, the latter are most commonly related to medical applications, particularly in medical devices, especially for devices to be inserted or implanted into the body. Furthermore, most commercial applications would not tolerate or desire erosion of the coating. Thus, the majority of powder coating applications for which antimicrobial agents would find utility are such that antimicrobial agents entombed within the bulk of the polymer coating matrix would not participate in and/or provide antimicrobial efficacy.

One known method of lessening the loss of antimicrobial agent due entombment is to dry blend the antimicrobial agent with the polymer particles before application. Such methods are taught in, e.g., Rei—U.S. Pat. No. 4,663,359 and Inoue—U.S. Pat. No. 4,629,645. However, mere dry blending of the prepolymer or polymer powder with the antimicrobial agent also has its misgivings. For example, in those dry blends where the antimicrobial particles are much smaller than the prepolymer and/or polymer particles, one is reliant upon Van der Waals forces and/or electrostatic charges to hold the former to the latter. However, due to the extremely weak nature of Van der Waals forces and electrostatic 'hold', separation and settling of the antimicrobial agent is typical, especially as a result of shaking, vibrations, etc. during shipping and handling as well as the forces imposed on the particles in preparation for and during the application of the powder coating material. Settling is even more pronounced in the absence of such forces or charges. Although the use of antimicrobial agents whose particle size is more similar to that of the powder coating particle will alleviate or lessen settling, it is not avoided altogether due to the differences in the density thereof relative to the density of the prepolymer and/or polymer particles. Specifically, prolonged shaking or vibrations as experienced in long haul transport or with long-term residence in a hopper will still allow for some settling to occur. While settling can be addressed, in part, by remixing the composition prior to application, it is unlikely that attempts to disperse the antimicrobial agent, particularly in the field, will be as successful as when the homogeneous blend was first made.

Furthermore, depending upon the coating thickness desired/needed and the natural/typical particle size of the antimicrobial agent selected, it is uncertain whether the specific application or powder coating process can tolerate the use of antimicrobial agents whose particle size is the same as or similar to that of the prepolymer and/or polymer particles. Even if such large particles can be tolerated, in order to maintain a given loading of the antimicrobial agent in the polymer coating—a critical limitation due to EPA labeling restrictions—one must inherently reduce the overall density of antimicrobial particles across the surface of the powder coated article of manufacture. Thus, with larger particles the antimicrobial active will have to travel further across the substrate surface to provide the same degree of bioefficacy as attained with a smaller particle sized material at the same loading. Depending upon the rate at which the active is released from the particles, the release may be insufficient to provide adequate protection across the whole surface of the substrate. Further, since many inorganic antimicrobial agents do not release the antimicrobial active but rely upon the bacteria coming into contact with the antimicrobial agent, the large spacing between particles will result in areas of no protection at all. Thus, in general, the use of large particle sized antimicrobial agents, particularly those that are comparable in size to the prepolymer and/or polymer particles, will tend to result in poorer bioefficacy.

Another concern with dry blends is that regardless of the particle size or the efficiency with which the dry blend is made, the difference in density between the antimicrobial agent and the prepolymer and/or polymer particles results in the two reaching the target surface at different rates. As a consequence, powder coatings prepared from dry blended antimicrobial powder coat compositions tend to manifest lower and notably non-uniform antimicrobial bioefficacy as a result of the formation of regions of high concentrations of the antimicrobial agent and regions of low or no antimicrobial agent.

Though it has not yet been seen in the powder coating art, theoretically speaking, solution bonding and/or binder compositions could possibly be employed as means to impregnate or coat the prepolymer or polymer particles with the antimicrobial additive. However, such is unlikely, especially from a practical or economical standpoint given the extremely small particle size of the powder coating particles themselves. For example, these methods entail additional, and oftentimes complex or costly, processing steps and the attendant capital equipment needs and longer processing time and, for solution impregnation, are only conceptually feasible for those antimicrobial agents that are sufficiently soluble and those prepolymer and polymer compositions that swell in the given solvent. Coating the powder coating particles with a binder composition containing the antimicrobial agent would require specialized apparatus and processes so as to ensure that the particles are individually coated without, or without significant, agglomeration of the coated particles. Furthermore, each of these theoretical processes introduces new and potentially costly concerns relative to environmental, health and safety matters.

Finally, Decker et. al., as mentioned above, suggest fusion bonding as a means of bonding the antimicrobial particles to the surface of the polymer powder particles. While effective, the bonding process is indiscriminate in that all the components are heated at the same time and to the same temperature. Consequently, not only is there bonding between the additive particles and the polymer particles but there is also substantial bonding between the polymer particles themselves. This has two disadvantages for powder coating applications. First, the agglomerated prepolymer and/or polymer particles must be separated from the remainder of the powder coating materials and/or subjected to further milling and/or grinding to rid the mixture of these large agglomerated particles. Otherwise, there is considerable concern for clogging the nozzles for application of the powder coating materials and/or an uneven powder coat will result on the treated surface. Secondly, areas of fusion between polymer particles are not available for depositing or adhering the antimicrobial agent. Besides the performance issues, these methods involve long processing times and heavy wear on the capital equipment resulting in lower production rates and shortened life of the mixing equipment as compared to dry blending of a loose mixture.

Thus, there remains a need for a simple process for successfully binding a solid polymer additive in particle form to the surface of prepolymer and/or polymer powder coating particles which avoids the use of additional chemical agents and additives, avoids or significantly mitigates concerns of agglomeration of the prepolymer and/or polymer particles, does not require the purchase and implementation of expensive/additional equipment, and can be accomplished at low cost with high throughput. In particular, there remains a need for a method of binding an antimicrobial agent to powder coating particles that fulfills the foregoing objectives.

Furthermore, there remains a need for a coating process that provides for a substantially uniform, high concentration of a solid polymer additive at the surface of the applied coating. In particular, there remains a need for a method of binding an antimicrobial agent to powder coating particles that fulfills the foregoing objective with minimal entombment of the antimicrobial agent and/or minimal loss of the antimicrobial agent from the surface of the powder coating particles prior to and/or during application to the substrate surface being coated therewith.

4. SUMMARY

The present invention provides for an improved method of fixedly coating powder coating prepolymer and/or polymer particles with microparticles of a solid, heat absorbing polymer additive material, especially antimicrobial additive materials. Broadly speaking, the improved method comprises heating a) the prepolymer and/or polymer powder coating particles to a temperature below that at which the surface of the particles begins to become tacky or manifest adherent properties and b) the microparticles of the solid, heat absorbing additive materials to a temperature at or above the temperature at which the prepolymer or polymer of the powder coating particles becomes tacky or begins to manifest adherent properties and allowing the heated additive material microparticles to become fixed to the surface of the prepolymer and polymer powder coat particles. Preferably, the prepolymer and polymer powder coating particles are heated to at least their Vicat temperature while the solid, heat absorbing microparticles are heated to a temperature of at least 10° C., preferably at least 20° C. above, most preferably at least 50° C. above, the temperature at which the prepolymer or polymer becomes tacky or begins to manifest adherent properties.

The process of the present invention is practiced in several ways. In one embodiment, the additive material microparticles and the prepolymer and/or polymer powder coating particles are heated in separate vessels and, subsequently, intimately mixed so as to allow the former to coat and become fixed to the surface of the latter. Mixing may be performed in a third vessel or, should the apparatus allow, the heated particles of one vessel may be added to those of the second vessel. In an alternate embodiment, the additive material microparticles and the prepolymer and/or polymer powder coating particles are intimately mixed prior to and/or concurrent with exposure to conditions which preferentially or selectively heat the former whereby the former are elevated to the desired temperature while the latter are only elevated to a temperature below that at which the surface of the particles begins to become tacky or manifest adherent properties.

The process of the present invention is applicable to the bonding of most any solid, heat absorbing additive material to the powder coating particles. For many solid additives the present invention provides an alternative to the process of melt blending/compounding as a means to integrate said additives into the prepolymer and/or polymer powder coating material prior to forming the powder. However, for those additives which are sensitive to the compounding conditions or to solvent type applications or which may undesirably affect the prepolymer or polymer matrix of the powder coating particle or the performance of the additive during or subsequent to its incorporation into the powder coating particle, the process of the present invention offers an improved and beneficial method or, in certain instances, the only means to effectively incorporate the additive into the powder coating composition, other than dry blending. The process of the present invention is especially suited for and provides a benefit relative to the formation of antimicrobial powder coating materials, most especially the formation of powder coating materials containing inorganic antimicrobial agents, particularly those that rely upon a release of the antimicrobial active agent for providing bioefficacy.

6. DETAILED DESCRIPTION

For purposes of clarification, the temperature at which the prepolymer or polymer "begins to manifest adherent properties" is that temperature at which the prepolymer or polymer begins to exhibit tack and is evidenced by the onset of agglomeration of the prepolymer or polymer particles: though it is recognized that the agglomeration, at this point, is minimal and readily broken with the application of light or minimal pressure such as simple touching or rolling the materials between one's fingers. This temperature may be, but is typically less than, the glass transition temperature (Tg) in the case of amorphous materials and the melt temperature in the case of crystalline materials. Further, unless otherwise stated herein, as used herein and in the appended claims the phrase "begins to manifest adherent properties" is also intended to include and reference physical entrapment: the latter referring to those circumstances where the prepolymer and/or polymer particles are heated to its Vicat temperature or to a temperature within about 5° C. (above or below) its Vicat temperature and the microparticles are heated to a temperature sufficiently higher than that of the prepolymer or polymer powder coating particles so that when the two are in forced contact with one another, the heat of the microparticles further softens the prepolymer or polymer material at the interface and becomes embedded therein, with or without an adhesive bond being formed, i.e., the heat of the microparticles may not be sufficient to actually melt the polymer at the interface with the prepolymer or polymer particle so as to form an adhesive bond. The forced contact may result from physical mixing or merely the compression experienced due to the weight of the mixture. Typically, the microparticles will be heated to a temperature that is at least about 10° C. higher, preferably at least about 20° C. higher, most preferably at least 50° C. higher, than that of the prepolymer or polymer particles and that is at least about 10° C., preferably at least 20° C., most preferably at least 50° C. above the Vicat temperature of the prepolymer and/or polymer particles. For the present invention, the Vicat temperature, more commonly known as the Vicat softening temperature, is determined according to ISO 306 (ASTM-D1525) using method is B50.

Additionally, unless contrary to or contradictory to the context in which they are used, it is to be understood that the terms "polymer particles", "prepolymer particles" and "prepolymer and/or polymer particles" are used interchangeably herein and in the appended claims and refer to polymer and/or prepolymer powder coating particles. In following, as noted below, the polymers may be thermoplastic or thermoset: though the invention is especially suited for use with thermoplastic polymers. Further, except as otherwise stated herein, reference herein to a particle size or particle size range means that at least 60%, preferably at least 80% and most preferably at least 95% of the particles meet the particular limitations. Finally, for the sake of simplicity, it is hereby affirmed that all patents and patent applications mentioned herein, specifically their teachings, are hereby incorporated herein, in their entirety, by reference.

In its broadest concept, the present invention provides an improved process for binding solid, heat absorbing polymer additive materials to prepolymer and/or polymer particles of powder coating compositions. In particular, the present invention provides an improved process for binding of solid micro- and nano-sized additive particles to micro-sized powder coating particles. Although the process may be employed for bonding most any solid additive material to the powder coating particles, it is especially suited for use in those circumstances where it is not desirable or not feasible to directly incorporate the solid additive into the polymer matrix concurrent with or prior to forming the powder coating polymer or prepolymer particles.

In its general embodiment, the process of the present invention comprises heating a) the prepolymer and/or polymer powder coating particles to a temperature below that at which the surface of the particles begins to become tacky or manifest adherent properties and b) the microparticles of the solid, heat absorbing additive materials to a temperature at or above the temperature at which the prepolymer or polymer of the powder coating particles becomes tacky or begins to manifest adherent properties and allowing the additive material microparticles to become fixed to the surface of the prepolymer and polymer powder coating particles. As discussed in greater detail further below, the process may be practiced in several ways. In one embodiment, the additive material-microparticles and the prepolymer and/or polymer powder coating particles are heated in separate vessels and, subsequently, intimately mixed so as to allow the former to coat and become fixed to the surface of the latter. Mixing may be performed in a third vessel or, should the apparatus allow, the heated particles of one vessel may be added to those of the second vessel. In an alternate embodiment, the additive material microparticles and the prepolymer and/or polymer powder coating particles are intimately mixed prior to and/or concurrent with exposure to conditions which preferentially or selectively heat the former whereby the former are elevated to the desired temperature while the latter are only elevated to a temperature below that at which the surface of the particles begins to become tacky or manifest adherent properties.

The process of the present invention is applicable to both thermoplastic and thermosetting prepolymer and/or polymer powder coating materials or compositions. Exemplary thermosetting powder coating materials/compositions include those comprising one or more curable or cross-linkable unsaturated polyester resins, epoxy resins, acrylic resins, phenol resins, melamine resins, urea resins, urethane resins, vinylether resins, etc.; mixtures of the foregoing resins and resins having a combination of the functional groups associated with thermosetting resins, including for example, epoxy-polyester resins, acrylic-urethane resins, and the like. For thermosetting powder coating compositions, the heat retentive solid additive, e.g., the antimicrobial agent, may be applied to particles of the neat thermosetting resin or to premix particles which comprise the thermosetting resin along with other typical ingredients of the powder coating including hardener or curing/cross-linking agent, colorants, stabilizers, fluidity agents, dispersants, antifoaming agents, thickeners, etc. Typically, though, the hardener or curing or cross-linking agent is present as or incorporated into another powder particle so as to remain isolated from the powder coating component with which it is reactive. Thermosetting powder coatings may cure or set through chemical reaction with a hardener or the like or cure or cross-lining may be induced by heat, actinic radiation (especially UV exposure), and the like. Such compositions are well known and widely available commercially.

Suitable thermoplastic polymer particles that may be prepared in accordance with the practice of the present invention include polyamides such as nylon 6, nylon 6,6, nylon 6,12; acrylics such as polymethylmethacrylate; polyolefins such as polyethylene, LLDPE, UHMWPE, and polypropylene; polyvinylalcohol; polyacetals; ABS resins; ethylene vinylacetate (EVA); polyesters such as polyethylene terephthalate and polybutylene terephthalate; polycarbonate; polyvinyl chloride; polyvinylidene chloride; polyvinylidene fluoride; polyetherether ketone (PEEK); polyphenylene oxide; styrene-acrylonitrile; polystyrene; polyester elastomers, polyurethane elastomers; polyacrylonitrile; etc. As with the thermosetting resin particles, the heat retentive, solid additive, e.g., the antimicrobial agent, may be applied to the neat resin particle or, more commonly, to particles of a compounded resin composition: the latter typically including stabilizers, fillers, colorants, etc.

Typical powder coating compositions (thermoplastic or thermosetting) have average particle sizes on the order of from about 5 to about 200 microns, more typically from about 20 to about 120 microns. Generally speaking, at least 60%, preferably at least 80%, of the powder coating particles will fall within 20 microns, most preferably, 10 microns, of the specified average particle size. In preferred powder coating compositions, 100% of the powder coating particles will be less than 200 microns, more preferably less than 120 microns, and at least about 40% of the particles will have a particle size of greater than 30 microns. Particle size and uniformity thereof is important for providing good coverage and a smooth uniform surface.

The present invention is applicable to most any solid, heat absorbing additive material in particle form provided that the composition and mass, including size, of the particle is capable of being heated to a temperature at or above, preferably above, that at which the polymer to which it is to be bonded "begins to manifest adherent properties" and is capable of retaining a sufficient amount of that heat until the prepolymer or polymer material/composition of the powder coating particles at the interface with the solid additive particle begins to manifest adherent properties. Certainly, the solid particle must be of a material or composition that is able to withstand the temperatures required for affecting the bond. Although there is essentially no limit on the materials, provided they meet the aforementioned limitations, the present invention is especially suited for use with inorganic solid particle materials. In particular, the present invention may be employed in adhering colorants, inorganic viscosity modifiers, fillers, flame retardants, catalysts, antimicrobial agents, sequestering agents, EMI/RFI shielding additives, and the like, especially antimicrobial agents, to the powder coating particles. Those skilled in the art, having the benefit of the teachings of this specification, will readily realize other specific additives for which this inventive process is applicable. All such additives are well known and widely available and, as new additives are developed, their suitability for use herein will also be readily apparent: Furthermore, each will be used in their conventional amounts consistent with the objectives to be attained by their use. However, as noted below, surprisingly, certain additives may be employed in amounts less than conventionally used when compounded into the polymer or prepolymer of the powder coating composition while maintaining the same or even improved performance.

The process of the present invention is especially of benefit with those polymer additives a) that are co-reactive with a component, by-product or contaminant of the prepolymer and/or polymer powder coating particle, particularly under the extreme conditions of melt blending, by that adversely affect the melt flow or physical properties of the powder coating, or c) whose performance or purpose is adversely affected by its incorporation into the polymer matrix or the process of incorporation. In the case of co-reactive materials, the processing conditions of the present invention are generally less severe than those of melt blending: thus, it may be that the conditions are not conducive to manifestation of co-reactivity. Where co-reactivity is still possible, the extent of the same is limited to the interface between the polymer particle and the solid particle. Other additives, especially inorganic additives like the flame retardant antimony oxide, tend to modify the melt flow characteristics of polymers into which they are incorporated. By bonding, rather than incorporating, them to the polymer particles, the melt flow characteristics of the powder coating composition as applied to the substrate surface is not affected thereby facilitating formation of a uniform powder coating. Finally, decorative additives as well as functional additives, including, for example, conductive particles for EMI/RFI shielding and/or for dissipating electrostatic buildup as well as antimicrobial additives, especially inorganic antimicrobial additives, may not be as efficacious or may require much higher loadings for their intended purpose when incorporated throughout the matrix of the powder coating particle as opposed to having a high concentration thereof at the surface of the powder coating particle. Specifically, as the polymer powder coating particles on the target surface melt and flow during the heating or baking step of the powder coating process, the high concentration of the additive borided to the outer, exposed surface thereof remains unaffected as the polymer melt flows beneath the additive. Upon completion of the heat/bake and subsequent, cooling cycles, the surface of the powder coating will have a substantially uniform, highly concentrated level of the additive across its exposed surface: essentially only that quantity of additive on the unexposed underside of the applied powder coating particles wilt be lost.

Generally speaking, the additive particles to be bonded to the polymer particles will typically be but a fraction of the size of the polymer particles to which they are to be bonded. Typically, they will be less than $1/10^{th}$ the size of the polymer particle, most likely less than $1/20^{th}$ the size. The smallest size is dependent largely upon the heat absorbing characteristics of the additive particles themselves. Certainly, if they are so small as to be unable to absorb and retain sufficient heat to enable the bonding, they are not suitable for use in the practice of the present invention. Obviously, this will vary from additive to additive depending upon the additive itself, its composition, density and heat absorptive characteristics. Typically, though, the smallest particle size for the solid additive will be on the order of about 10 nanometers, preferably at least 100 nanometers, most preferably no less than 1 micron.

As mentioned, the present invention is especially suited for use in preparing antimicrobial polymer and prepolymer powder coating materials. Preferred antimicrobial agents are those that contain an antimicrobial metal or metal ion. Examples of such metals or metal ions include silver, copper, zinc, tin, gold, mercury, lead, iron, cobalt, nickel, manganese, arsenic, antimony, bismuth, barium, cadmium, chromium and thallium and their respective ions. Silver, copper, zinc, and gold, especially their ions, as well as combinations thereof, especially silver and copper or zinc or both, are preferred because they are considered safe for in vivo use. Silver, particularly ionic silver and/or nano-silver, is more preferred due to the fact that silver has the highest ratio of efficacy to toxicity, i.e., high efficacy to low toxicity; though combinations of silver and copper have recently been shown to have improved efficacy and/or color stability as compared to silver alone.

The antimicrobial agent can also be in the form of simple salts and organometallic compounds of the antimicrobial metals such as the oxide, sulfide, chloride, bromide, carbonate, nitrate, phosphate, dihydrogen phosphate, sulfate, oxalate, acetate, benzoate, thiosulfate and the like. Specific examples include silver nitrate, cupric oxide, zinc acetate and zinc oxide. More recent attention has focused on the organometallic compounds derived from silver and various carboxylic acids, especially citric acid, acetic acid and the like, including silver citrate, silver dihydrogen citrate, tri-silver citrate and the like. Especially preferred are the silver citrates prepared though electrolysis as shown in Arata et. al:, (U.S. Pat. Nos. 6,197,814, 6,583,176, and US 2005/0245605). Although simple salts and organometallic compounds are useful, they tend to be short lived due to quick and/or essentially uncontrolled dissolution.

Alternatively, the antimicrobial agent may be in the form of a water soluble glass containing the antimicrobial agent or compound. Suitable antimicrobial water soluble glasses include those disclose in U.S. Pat. No. 5,470,585. By suitable adjustment of the glass composition, the dissolution rates in water can be controlled, thereby extending their longevity.

Preferably, the antimicrobial agent will be in the form of an ion-exchange type antimicrobial agent, alone or in combination with one or more other antimicrobial agents. Ion-exchange type antimicrobial agents are typically characterized as comprising a ceramic particle having ion-exchanged antimicrobial metal ions, i.e., the antimicrobial metal ions have been exchanged for (replaced) other non-antimicrobially effective ions in the ceramic particles. Additionally these materials may have some surface adsorbed or deposited metal; however, the predominant antimicrobial effect is as a result of the ion-exchanged antimicrobial metal ions.

Antimicrobial ceramic particles include, but are not limited to zeolites, hydroxyapatite, zirconium phosphates and other ion-exchange ceramics. These ceramic materials come in many forms and types, including natural and synthetic forms. For example, the broad term "zeolite" refers to aluminosilicates having a three dimensional skeletal structure that is represented by the formula: $XM_2/nO$—$Al_2O_3$—$YSiO_2$-$ZH_2O$ wherein M represents an ion-exchangeable ion, generally a monovalent or divalent metal ion; n represents the atomic valency of the (metal) ion; X and Y represent coefficients of metal oxide and silica, respectively; and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange antimicrobial agents may incorporate most any antimicrobial metal ions, including those mentioned above. Most commonly, though, silver ions or silver ions in combination with zinc and/or copper ions are used. The amount of antimicrobial metal ion is generally in the range of from about 0.1 to about 25 wt %, preferably from about 0.3 to about 20 wt %, most preferably from about 2 to about 10 wt %, based upon 100% total weight of ceramic carrier. Where other antimicrobial metal ions are present, the makeup will be from about 0.1 to about 15 wt % of silver ions and from about 0.1 to about 15 wt % of copper and/or zinc ions. These ion-exchange type antimicrobial agents may also have incorporated therein ion-exchanged ammonium ion for improved color stability. If present, the ammonium ion may be present at a level of up to about 20 wt % of the carrier; however, it is desirable to limit the content of ammonium ions to about 0.5 to about 2.5 wt %

All of the foregoing ion-exchange type antimicrobial agents are widely available and well known to those skilled in the art. Hydroxyapatite particles containing antimicrobial metals are described, e.g., in U.S. Pat. No. 5,009,898 Zirconium phosphates containing antimicrobial metals are described, e.g., in U.S. Pat. Nos. 5,296,238; 5,441,717 and 5,405,644. Antimicrobial zeolites containing antimicrobial metal ions are described in, e.g., U.S. Pat. Nos. 4,911,898; 4,911,899 and 4,938,958. Especially preferred ion-exchange antimicrobial agents are the antimicrobial zeolites available from AgION Technologies, Inc., of Wakefield, Mass., USA including, but not limited to the following product numbers: AW10D (0.6% by weight of silver ion-exchanged in Type A zeolite particles having a mean average diameter of about 3µ), AG10N and LG10N (2.5% by weight of silver ion-exchanged in Type A zeolite particles having a mean average diameter of about 3µ and 10µ, respectively); AJ10D (2.5% silver, 14% by weight zinc, and between 0.5% and 2.5% by weight ammonium ion-exchanged therein in Type A zeolite having a mean average diameter of about 3µ); AK10D (5.0% by weight of silver ion-exchanged in Type A zeolite particles having a mean average diameter of about 3µ) and AC10D (6.0% by weight of copper and 3.5% by weight silver ion-exchanged in Type A zeolite particles having a mean average diameter of about 3µ).

In accordance with the present invention, the thermosetting or thermoplastic polymer or prepolymer particles and the particles of the heat retentive/absorptive additive material to be combined-therewith are to be heated to two different temperatures. Specifically, the polymer or resin particles are heated to a temperature below that at which the surface of the particles begins to become tacky or manifest adherent properties. Preferably, the prepolymer and polymer particles are heated to at least their Vicat temperature but less than, preferably 2° C. to 5° C. less than, the temperature at which they begin to become tacky or manifest adherent properties.

The microparticles of the solid, heat absorbing additive materials, on the other hand, are heated to a temperature that is sufficiently higher than that of the prepolymer or polymer particles, based on its physical, heat absorptive, and heat transfer properties, so that when the two are in intimate contact with one another, preferably in forced contact, the heat transfer from the microparticles to the prepolymer or polymer particle at the point of contact is sufficient to cause the latter to become tacky or manifest adherent properties, thereby adhesively or fixedly binding the microparticles to the surface or within the surface layer of the prepolymer or polymer particles. Typically, the microparticles of the solid, heat absorbing additive material will be heated to a temperature that is at least about 10° C., preferably at least about 20° C., most preferably at least about 50° C., above the temperature at which the prepolymer or polymer of the powder coating particles begins to become tacky or manifest adherent properties.

Of course the actual temperature to which the solid heat absorbing microparticles of the additive material are to be raised will depend upon a number of different factors and variables including the temperature differential between the temperature at which the surface layer of the prepolymer powder coating particles begin to become tacky or manifest adherent properties and the actual temperature to which they are raised as well as the mass, the shape or geometry (especially surface area to mass ratio), the heat absorptive properties, and the heat transfer or heat loss characteristics of the microparticles of the solid heat absorbing additive material. For example, with respect to the latter, particles of large surface area to mass (i.e., one in a flake or fibrous form) will loose heat much more quickly and, therefore, may necessitate their heating to a higher temperature than may be necessary for a microparticle of the same material and mass but a smaller surface area (e.g. a spherical or spheroid form). Similarly, particles of larger mass but the same composition will retain heat better than those of smaller mass and, thus, have more heat energy to transfer to the polymer particle to create the bond. Further, density and heat absorptive characteristics of composition of the microparticles of the additive materials will also vary. For example, microparticles of a metal such as steel would not require the same temperature elevation as similarly shaped and sized microparticles of a ceramic material. Here, the former may only require a temperature elevation of, for example, 5° C. to 10° C. above the temperature at which the prepolymer or polymer of the powder coating particles begin to become tacky or manifest adherent properties, whereas the latter may require a temperature elevation of 40° C. to 50° C. or higher. Simple experimentation will enable one to select the proper temperature elevation needed for the chosen form and mass of the solid, heat absorbing microparticle additive material.

Bonding of the microparticles of the solid heat absorbing additive materials to the powder coating polymer or resin particles occurs as a result of or is facilitated by a heat transfer from the former to the latter. Specifically, when the solid, heated additive microparticle comes into contact with the polymer or prepolymer powder coating particle, the monolayer, or at least a portion thereof, of polymer or prepolymer at the interface of the additive microparticle and the polymer or prepolymer powder coating particle is heated to a temperature at or above that at which it becomes tacky or begins to manifest adhesive characteristics whereby the additive microparticle becomes bonded or adhered to the surface of the polymer or prepolymer powder coating particle. Alternatively, the heat transfer may be sufficient so that the surface monolayer of the powder coating particle, or at least a portion thereof, is sufficiently softened whereby the additive microparticle becomes embedded in the softened monolayer, with or without true adhesion.

The process of the present invention may be employed in a batch type operation or in a continuous operation. The batch processing is especially suited for those polymers having high glass transition or melt temperatures due to the higher temperature demands of the process. Even so, with proper configuration of the apparatus, continuous processing is also possible.

In batch processing pre-determined quantities of the two components are heated to the appropriate temperatures and mixed together in a mixing vessel that is preferably configured to provide continuous heating and intimate mixing or blending of the two components. For example, the vessel is preferably maintained at or near the same temperature as that to which the polymer material is elevated. By maintaining the mixing vessel and the contents therein at an elevated temperature, one prevents the loss of too much heat from the microparticles to the atmosphere and, consequently, the failure of the same to bond to the polymer particles. Additionally, it is to be understood that somewhat higher mixing vessel temperatures could be used, especially where the heated prepolymer and/or polymer particles are added to the heated additive particles or where both are added gradually, with intermixing upon addition, into a third vessel, since the microparticles will coat the polymer particles and prevent substantial bonding of the polymer particles to the vessel walls and/or mixer components from occurring.

The materials in the mixing vessel will preferably be subjected to continuous mixing, agitation or tumbling. A stir means or auger-like means may be employed to provide continuous mixing or agitation. Alternatively, a mixer vessel which rotates, with or without projections, especially spiraling or thread-like projections, on the inner surface wall of the vessels extending into the inner volume of the vessel, may be used for providing continual tumbling, much like a cement mixer. Mixing of the two components will ensure good dispersion of the one in and about the other so as to allow for a more even coating of the polymer and prepolymer powder coating particles with the solid additive microparticles; similar, if you will, to the coating of granulated sugar with powdered cinnamon.

For optimizing the throughput of the batch processing, it is preferable to heat the two components and combine the same in a third mixing vessel. In this manner, the components for the next process batch may be heated as the components of the present batch are being mixed. However, it is also contemplated that the mixing may occur in the vessel or chamber in which one of the two components is heated. Preferably, in this embodiment, the heated additive microparticles are gradually added to the vessel or chamber containing the heated polymer and prepolymer powder coating particles with constant mixing, agitation or tumbling so as to more evenly disperse the former over the latter; again, thereby providing more uniform coverage.

In yet another embodiment of the batch processing, the two components may be intimately mixed prior to or concurrent with heating and the mixture heated using microwave energy, induction heating (e.g., electromagnetic energy), or another suitable means which selectively and/or preferentially heats the additive microparticles as opposed to the polymer and prepolymer powder coating particles. For example, the mixture may be subjected to microwave energy wherein the compositional make-up of the solid additive microparticles is such that they absorb the microwave energy faster and/or more efficiently than the polymer particles thereby elevating them above the temperature at which the prepolymer or polymer "begins to manifest adherent properties" before the polymer particles themselves reach their glass transition temperature or melt temperature, as appropriate. This method may be more energy efficient since one is not reliant upon conductive heating which oftentimes requires that the mixing vessels and associated equipment/components are also heated.

As noted, the present process is also capable of continuous operation. Here, for example, two feeder inlets supply constant flows of the heated polymer or resin powder coating particles and the heated heat absorbing additive microparticles to a mixing chamber, preferably heated, where the two are brought into intimate contact with one another and then exit from the mixing chamber through an outlet means. Intimate mixing of the two components may occur as a result of the intersecting of the flow streams and/or the cascading and tumbling thereof as they fall in the mixing chamber and progress into or on, as appropriate, the exit means. For example, the mixing chamber may have a series of cascading tilted shelves that cause the mixture to cascade back and forth as the materials fall through the mixing chamber to a catch basin, which then captures the mixture and passes it out of the mixing chamber. Alternatively, the mixing chamber may comprise a mixing or stir means or an auger-like means for mixing the components as they pass through the mixing chamber: passage through the mixing chamber being facilitated by a conveyance means that moves the mixture towards the exit. The conveyance means may be a belt or an auger-like device: the latter also providing mixing. Alternatively, the mixing chamber may rotate and have one or more screw-like or thread-like elements on the inner surface thereof that increases the mixing and-progression of the materials through the mixing chamber. In yet another embodiment, the rotating mixing chamber may be titled with a series of shelves, circular projections or reverse screw-like or thread-like projections that impeded the movement of the particles from the top of the chamber to the bottom thereof such that progression occurs as a result of the spillover of the particles from one projection to the next.

As with the batch apparatus, the mixing chamber and/or elements thereof are preferably maintained at an elevated temperature so as to preclude too much heat loss from the additive microparticles before intimate mixing and bonding is attained with the polymer powder coating particles. Absent a configuration that ensures mixing of the two components before the polymer powder coating particles come into contact with the surface and/or elements of the mixing chamber, the temperature of the mixing chamber is preferably maintained below that temperature at which the polymer particles begin to manifest adhesive characteristics. Otherwise, the surfaces should be composed of or be treated with a material to which the prepolymer and/or polymer particles will not adhere.

Generally speaking, any suitable heating means may be employed, for example heating may be by convection, conduction, induction, or by irradiation, including IR or, as noted above, microwave. Conductive heating is most common. In batch processing the walls of the vessels are heated. In continuous processing, the vessels or chambers which hold the materials before they are fed to the mixing chamber and/or the conduits themselves which transport the particles to the mixing chamber may have heated surfaces.

As mentioned above, the mixing vessel or chamber is preferably heating during the mixing step. Although lower temperatures are possible, it is preferable that the temperature of the mixing chamber be no less than, and more preferably at least 5° C. to 10° C. higher than, the Vicat temperature of the prepolymer and/or polymer particles, but less than, preferably at least 2° C. to 5° C. less than the temperature at which the prepolymer or polymer begins to become tacky or manifest adherent properties. By maintaining an elevated temperature within the mixing chamber or vessel, one minimizes concern for heat loss to the environment or surfaces of the mixing vessel or chamber. Obviously, it is a necessary objective of the process of the present invention to maintain sufficient absorbed heat in the components during the mixing step so as to ensure that the heat loss or, more appropriately, heat transfer upon contact of the additive particle and the prepolymer and/or polymer particle is sufficient to cause the prepolymer or polymer composition to begin to manifest adherent properties so as to created a tack or pre-bond and then continue to lose heat to form a formal bond: one that is not broken under the continued mixing conditions. In the preferred embodiments, the heat of the particles will be sufficient to melt or liquefy the polymer at the additive/polymer particle interface with the concurrent transfer/loss of heat so that the prepolymer or polymer material re-solidifies.

Optionally, the coated polymer particles upon exiting the mixing vessel of the batch processing apparatus or the mixing chamber of the continuous processing apparatus will be subjected to a screening so as to separate the free additive microparticles from the coated particles. The free additive microparticles may then be re-used in a subsequent coating process.

Although agglomeration is unlikely or will be significantly reduced by the practice of the present invention, it may also be desirable to subject the coated particles to a screening process to separate any agglomerated polymer particles from the coated particles. Any agglomerated particles may then be subjected to milling or crushing to separate the polymer particles and recombined with the treated particles or returned to the heating chamber for a second treatment. Unlike the polymer-to-polymer particle agglomeration of the fusion bonding method of the prior art, any agglomeration found with the present invention is likely to be as a result of the additive particles bridging the polymer particles. Such bonds are likely to be markedly weaker than with the polymer-to-polymer bonds and, thus, readily reversed with minimal effort.

As noted above, the present invention is applicable to the coating of powder coating particles with most any solid additive therefore; however, it is especially applicable to and desirous for the preparation of antimicrobial powder coatings, particularly antimicrobial powder coating compositions wherein the polymer powder is a hydrophobic or poorly hydrophilic polymer and the antimicrobial agent is one that requires the presence of moisture/water for release of the antimicrobial active agent. Again, as discussed above, many inorganic antimicrobial agents, including those based upon metals or metal ions, metal salts, antimicrobial dissolving glasses and the like, rely upon water to generate and/or dissolve the antimicrobial active agent or, in the case of the ion-exchange type antimicrobial agents, enable the exchange and transport of the antimicrobial metal ions. When these antimicrobial agents are compounded into the prepolymer or polymer composition during the formation of the powder coating particles, a significant impact on bioefficacy and longevity is manifested in the powder coating as applied to a substrate when the polymer comprising the powder coating is hydrophobic or poorly hydrophilic. Since water cannot effectively penetrate the polymer coating, those particles of the antimicrobial agent within the bulk of the polymer are not available to provide antimicrobial performance, in the case of hydrophobic polymers, or to provide a sufficient level of antimicrobial release, in the case of poorly hydrophilic polymers. Thus, in these powder coating compositions, a large weight percent of the antimicrobial agent is not available to provide bioefficacy. In contrast, essentially all of the antimicrobial agent on the exposed surface of the particles made in accordance with the present invention, once applied to the target surface, is available.

When the powder coating is applied to a substrate surface, the polymer matrix of the particles will flow and fuse with adjacent particles. This action will expose some of the antimicrobial particles at and near the exposed surface of the particle; however, the majority of the antimicrobial agent is still entombed within the polymer matrix of the formed powder coating. In contrast, when the powder coating composition of the instant invention is applied to a substrate, the high concentration of the antimicrobial surface remains and essentially only that on the unexposed surface of the particle is trapped. Thus, one can use much less antimicrobial agent than necessary with conventional compounding methods to achieve the same level of bioefficacy.

One method to overcome this problem with powder coating compositions wherein the antimicrobial agent is into polymer or prepolymer of the powder coating particle is to increase the amount of the antimicrobial agent. This increases the concentration and, hence, the likelihood that any given particle of the antimicrobial agent will be at or near the exposed surface of the powder coating particle at the time of application to the substrate. However, given the relatively high costs of these antimicrobial agents, especially the ion-exchange type, there is much more waste and lost value in these conventionally compounded powder coatings. Thus, antimicrobial powder coatings made in accordance with the present invention can achieve an equivalent if not much higher level of bioefficacy and/or longevity with less antimicrobial agent than conventional compounding methods. Furthermore, in the United States and elsewhere around the world, government regulations limit the amount of antimicrobial-agent that may be incorporated into different products. Thus, one is much more limited in terms of the maximum concentration of antimicrobial agent that may be achieved at the powder coating surface by conventionally compounded powder coatings as compared to those made in accordance with the present invention.

Figure 1:
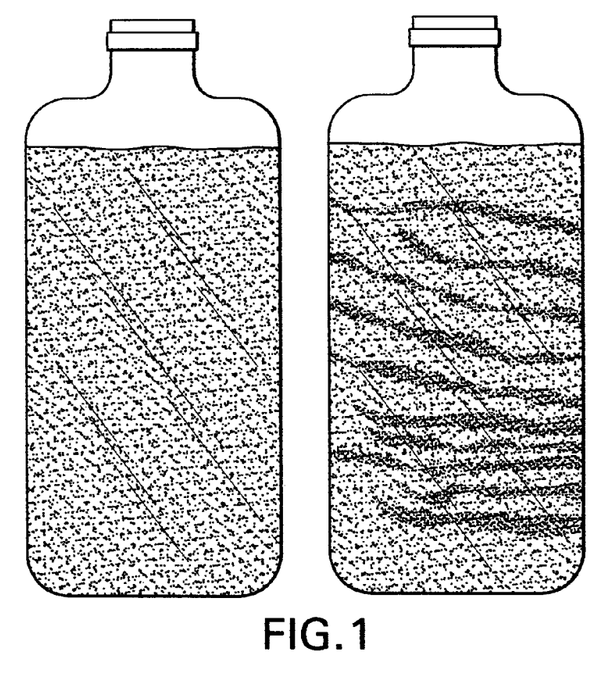
FIG. 1 is a drawing depicting the inventive composition and a comparative composition following tap vibration for 5 minutes.
Figure 2:
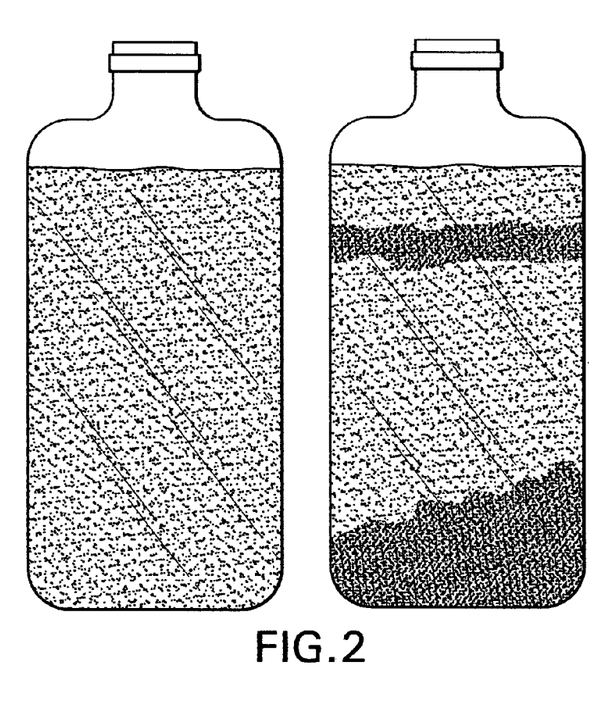
FIG. 2 is a drawing depicting the compositions of FIG. 1 following tap vibration for 3 hours.

Rather than adding more antimicrobial agent, another option for addressing the aforementioned problem with powder coatings having the antimicrobial agent compounded into the polymer or prepolymer of the powder coating particle is to merely dry blend the prepolymer and polymer powder coating particles with the antimicrobial agent. Like the powder coating compositions made in accordance with the present invention, more antimicrobial agent is available since none is within the polymer; however, because of the mass differences (density and/or size) between the antimicrobial agent and the powder coating particle, there is a high tendency for the two constituents to separate. For example, FIGS. 1 and 2 show two vials, each vial containing an antimicrobial thermoplastic powder coating formulation containing about 9 wt % AgION AJ10D-silver zeolite antimicrobial agent (average particle size ~3µ) from AgION Technologies, Wakefield, Mass. 01880, and about 91% of Plastcoat NG10 polyethylene powder coating composition (95% below 300µ particle size, 80° C. Vicat temperature and 107° C. melting point) from Plastcoat, Cleveland, Ohio. The composition on the left was made in accordance with the practice of the present invention. Specifically, the silver zeolite was heated at 300° C. for 60 minutes and the polyethylene powder heated at 100° C. for 60 minutes. The heated silver zeolite was then added to and mixed with the polyethylene powder to coat the same. The composition on the right was made by simply forming an intimate mixture of the two wherein the silver zeolite was substantially, homogeneously intermixed with the polyethylene powder. The compositions were placed in vials and the vials shaken on a sieve tapper for about five minutes (FIG. 1) and 300 minutes (FIG. 2). As seen, those formulations made by dry blending showed a progressive separation of the two constituents: the degree and extent of separation increasing with longer and longer shaking times. On the other hand, no separation was seen in the composition according to the present invention.

Although this test was conducted on a mechanical shaker, these results are consistent with what would be expected when such formulations are subjected to vibration and shock in transport, storage and use. Thus, unless the dry blended formulations were subsequently remixed immediately prior to use, a substrate surface coated with these antimicrobial powder coating compositions would have areas of little to no antimicrobial performance. Additionally, there would be a marked effect on the physical properties and/or appearance of the formed polymer powder coating itself, consistent with the high concentration of the antimicrobial additive in other areas. For example, one may expect discoloration due to the high concentration of silver and/or loss of physical integrity of the coating due to the high loading of "filler" material that interrupts the polymer network and, hence, properties/strength.

The powder coating compositions of the present invention may be applied to any substrates using conventional methods including spray coating, electrostatic deposition, flame coating, etc. In the case of thermosetting powder coating compositions, cure thereof will be effectuated by conventional methods of cure for the type of thermosetting composition employed. For example, heat curable powder coatings will be cured by baking the coated article for sufficient period of time to effect cure. UV curable compositions will be cured by exposure to UV light, alone or in combination with heat, for a sufficient period of time to effectuate cure. Similarly, thermoplastic powder coatings will be subjected to heat concurrent with and/or following application to the substrate to effectuate flow and fusion of the powder coating materials to form the uniform or substantially uniform coating before removing the heat to allow the same to cool and solidify. In addition to or as part of the powder coating method chose, the substrate may, be induced to carry an electric charge to facilitate electrostatic deposition and/or heated to help tack weld the powder coating particles to the surface during application. All such methods of application and cure or set are convention and well known to those skilled in the art.

Although the present invention has been described with respect to the specific embodiments mentioned above, it should be appreciated that other embodiments utilizing the concepts of the present invention are possible without departing from the scope of the invention. Thus, the present invention is defined by the claimed elements and any and all modifications, variations, or equivalents that fall within the spirit and scope of the underlying principles set forth herein.

We claim:

1. A method of fixedly coating (a) powder coating prepolymer and/or polymer particles, individually and collectively, the polymer particles, with (b) microparticles of a solid, heat absorbing polymer additive material, said method comprising i) heating the polymer particles to a temperature below that at which the surface of the polymer particles begins to become tacky or manifest adherent properties, (ii) separately heating the microparticles of the solid, heat absorbing additive material to a temperature 5° C. or more above the temperature at which the prepolymer or polymer of the polymer particles becomes tacky or begins to manifest adherent properties, (iii) bringing the separately heated particles into contact with each other, and (iv) allowing the microparticles of the solid, heat absorbing additive material to become fixed to the surface of the polymer particles as a result, in whole or in part, of the transfer of heat energy from the higher temperature additive material particles to the surface of the polymer particles at their point of contact.

2. The method of claim 1 wherein the heated particles of the heat absorbing additive material contain sufficient heat whereby upon contact with the surface of the polymer particles the heat transfer from the microparticles of the heat absorbing additive material to the polymer particles at the point of contact causes the latter, at the point of contact, to become tacky or manifest adherent properties.

3. The method of claim 1 further comprising the step of intimately mixing the microparticles of the solid, heat absorbing additive material with the polymer particles.

4. The method of claim 3 further comprising the step of heating the mixture as it is being mixed using a heating means that is selective for or preferential to the microparticles of the heat absorbing additive material whereby the heat absorbing additive material is heated to or maintained at a temperature at or above the temperature at which the prepolymer or polymer of the polymer particles becomes tacky or begins to manifest adherent properties while maintaining the temperature of the polymer particles at a temperature below that at which the polymer particles begins to become tacky or manifest adherent properties.

5. The method of claim 1 wherein the polymer particles are heated to or within five degrees centigrade of their Vicat temperature and the microparticles of the heat absorbing additive material are heated to a temperature at least 10° C. higher than the Vicat temperature of the polymer particles.

6. The method of claim 1 wherein the polymer particles are heated to a temperature that is above the Vicat temperature and at least 2° C. lower than the temperature at which the polymer or prepolymer begins to manifest adherent properties.

7. The method of claim 6 wherein the microparticles of the heat absorbing additive material are heated to a temperature that is at least 20° C. higher than the temperature at which the prepolymer or polymer begins to manifest adherent properties.

8. The method of claim 6 wherein the microparticles of the heat absorbing additive material are heated to a temperature that is at least 50° C. higher than the temperature at which the polymer particles begin to manifest adherent properties.

9. The method of claim 6 wherein the polymer particles are heated to a temperature that is at least 5° C. lower than the temperature at which the polymer or prepolymer begins to manifest adherent properties.

10. The method of claim 1 wherein the average particle size of the polymer and prepolymer powder coating particles is from 5 to 200μ.

11. The method of claim 1 wherein the average particle size of the heat absorbing polymer additive is no more than $1/10^{th}$ that of the powder coating particles.

12. The method of claim 1 wherein the average particle size of the heat absorbing polymer additive is no more than $1/20^{th}$ that of the powder coating particles.

13. The method of claim 1 wherein the heat absorbing additive is selected from the group consisting of colorants, inorganic viscosity modifiers, fillers, flame retardants, catalysts, antimicrobial agents, sequestering agents, and EMI/RFI shielding additives.

14. The method of claim 1 wherein the powder coating prepolymer or polymer is a thermoset and the heat absorbing additive is a catalyst for the cure or cross-linking thereof.

15. The method of claim 1 wherein the heat absorbing additive is an antimicrobial agent selected from antimicrobial metals, antimicrobial metal salts, ion-exchange type antimicrobial agents having ion-exchange antimicrobial metal ions and soluble glass particles having incorporated therein antimicrobial active agent in the form of an antimicrobial metal, metal salt, or metal ion.

16. The method of claim 15 wherein the antimicrobial agent is present as nano-particles of an antimicrobial metal or salt.

17. The method of claim 1 wherein the heat absorbing additive is an ion-exchange type antimicrobial agent having ion-exchanged antimicrobial silver, copper, or zinc ions or combinations of any two or all three of said ions.

18. A method of fixedly coating (a) powder coating prepolymer and/or polymer particles, individually and collectively, the polymer particles, with (b) microparticles of a solid, heat absorbing polymer additive material, said method comprising i) mixing the two types of particles together and ii) concurrently, subsequently or while continuing to mix, heating the mixture using a heating means that is selective for or preferential to the microparticles of the heat absorbing additive material whereby the heat absorbing additive material is heated to a temperature 5° C. or more above the temperature at which the prepolymer or polymer of the polymer particles becomes tacky or begins to manifest adherent properties without raising the temperature of the polymer particles to a temperature at or above which the polymer particles begins to become tacky or manifest adherent properties, and iii) allowing the microparticles of the solid, heat absorbing additive material to become fixed to the surface of the polymer particles as a result, in whole or in part, of the transfer of heat energy from the higher temperature additive material particles to the surface of the polymer particles at their point of contact.

19. The method of claim 18 wherein the combination of the particles is continuing to be mixed while being heated.

20. The method of claim 18 wherein the heat absorbing additive is an antimicrobial agent selected from antimicrobial metals, antimicrobial metal salts, ion-exchange type antimicrobial agents having ion-exchange antimicrobial metal ions and soluble glass particles having incorporated therein antimicrobial active agent in the form of an antimicrobial metal, metal salt, or metal ion.

* * * * *